US008323925B2

(12) United States Patent
Chakravarthy

(10) Patent No.: US 8,323,925 B2
(45) Date of Patent: Dec. 4, 2012

(54) Aβ-BINDING PROTEIN AND ITS PEPTIDE DERIVATIVES AND USES THEREOF

(76) Inventor: Balu Chakravarthy, Ottawa (CA)

( * ) Notice: Subject to any disclaimer, the term of this patent is extended or adjusted under 35 U.S.C. 154(b) by 876 days.

(21) Appl. No.: 11/921,219

(22) PCT Filed: Jun. 16, 2006

(86) PCT No.: PCT/CA2006/000990
§ 371 (c)(1),
(2), (4) Date: Mar. 18, 2009

(87) PCT Pub. No.: WO2006/133566
PCT Pub. Date: Dec. 21, 2006

(65) Prior Publication Data
US 2011/0300141 A1 Dec. 8, 2011

Related U.S. Application Data

(60) Provisional application No. 60/691,248, filed on Jun. 17, 2005.

(51) Int. Cl.
C12P 21/06 (2006.01)
C04B 24/26 (2006.01)
G01N 33/53 (2006.01)
(52) U.S. Cl. ............ 435/69.1; 524/2; 435/7.71
(58) Field of Classification Search ............ None
See application file for complete search history.

(56) References Cited

U.S. PATENT DOCUMENTS 5,385,915 A 1/1995 Buxbaum et al.

FOREIGN PATENT DOCUMENTS

| WO | WO01/88088 | 11/2001 |
| WO | WO 02/086122 | 10/2002 |
| WO | WO/03/062391 | * 7/2003 |

OTHER PUBLICATIONS

Collins, Generation and initial analysis of more than 15,000 full-length human and mouse cDNA sequences., Proc Natl Acad Sci U S A. (2002), vol. 99(26), pp. 16899-16903.*
PCM1 protein (last viewed on Jan. 9, 2012).*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*

(Continued)

Primary Examiner — Alexander Kim
(74) Attorney, Agent, or Firm — Johanna Coults; Cassan Maclean

(57) ABSTRACT

A protein kinase C inhibitor that binds β-amyloid and its peptide derivatives with the same function are disclosed. These may be useful in the treatment of Alzheimer's disease, for example as pseudo vaccines comprising antibodies, or as part of fusion proteins which are able to pass through cell membranes or through the blood-brain barrier. Methods of using the PKC inhibitor and its peptide derivatives for treating Alzheimer's disease are also disclosed.

20 Claims, 11 Drawing Sheets

A.

B.

C.

OTHER PUBLICATIONS

Wacey et al., Disentangling the perturbational effects of amino acid substitutions in the DNA-binding domain of p53., Hum Genet, 1999, vol. 104, pp. 15-22.*

Abulrob et al., The blood—brain barrier transmigrating single domain antibody: mechanisms of transport and antigenic epitopes in human brain endothelial cells, Journal of Neurochemistry (Nov. 2005) vol. 95, Issue 4, pp. 1201-1214.*

Van Geel, M. et al., Genbank Accession No. AAK21980, Jul. 1, 2001.

Friedman, L.M. et al., Nat. Toxins 1997, vol. 5, pp. 173-179, ISSN 1056-9014.

Golde, T.E., "Alzheimer disease therapy: Can the amyloid cascade be halted?", J. Clin. Invest. 111, 2003, pp. 11-18.

Monsonego A. et al., "Immunotherapeutic approaches to Alzheimer's disease", Science 302, 2003, pp. 834-838.

Bard F. et al., "Peripherally administered antibodies against amyloid beta-peptide enter the central nervous system and reduce pathology in a mouse model of Alzheimer disease", Nat. Med. 6, 2000, pp. 916-919.

Joliot A. et al., "Transduction peptides: from technology to physiology", Nat. Cell Biol. 6, 2004, pp. 189-196.

Zhao M. et al., "Intracellular cargo delivery using tat peptide and derivatives", Med. Res. Rev. 24, 2004, pp. 1-12.

D'Andrea M.R. et al., "Consistent immunohistochemical detection of intracellular beta-amyloid 42 in pyramidal neurons of Alzheimer's disease entorhinal cortex", Neurosci. Lett. 333, 2002, pp. 163-166.

McLean C.A. et al., "Soluble pool of Abeta amyloid as a determinant of severity of neurodegeneration in Alzheimer's disease", Ann. Neurol. 46, 1999, pp. 860-866.

* cited by examiner

FIGURE 2
A.
PK-4
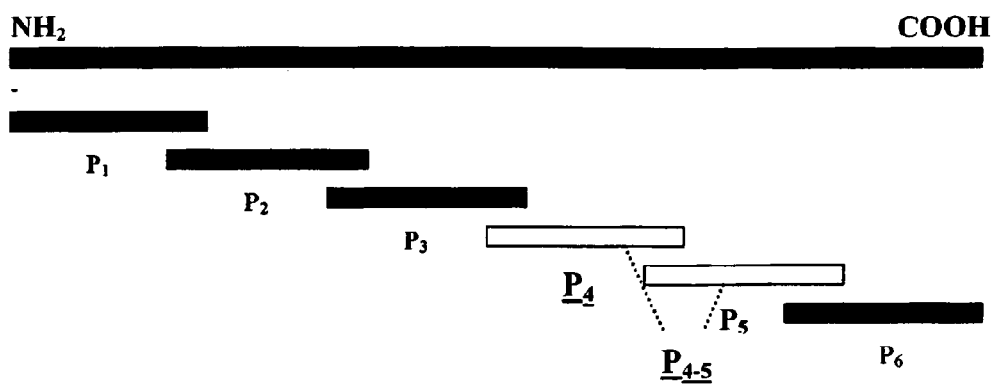
B: Dot Blot
Peptide p4 binding to Aβ (5μg)
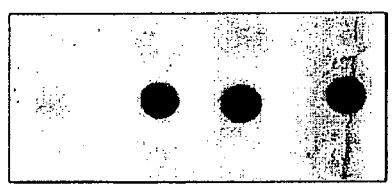
P4    0    100    200    400    nM
Peptide p5 binding to Aβ
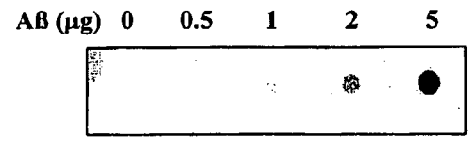
p5    200nM

FIGURE 9
Saline
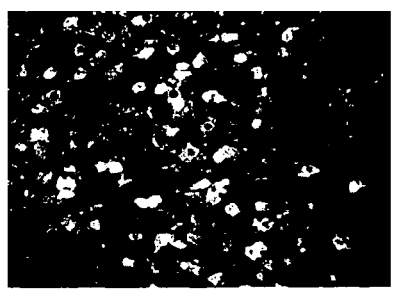
P₄
P₅
P₄₋₅

FIGURE 12
A
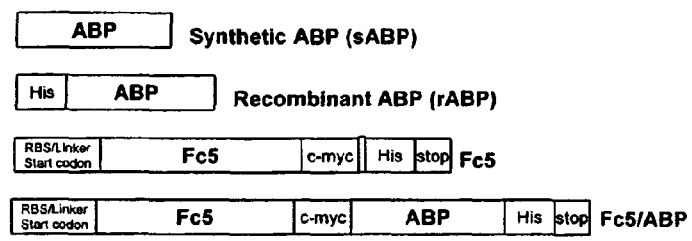
B
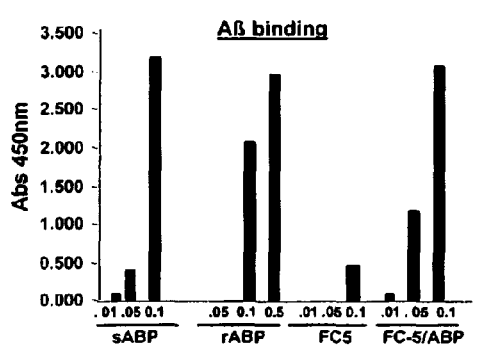
C
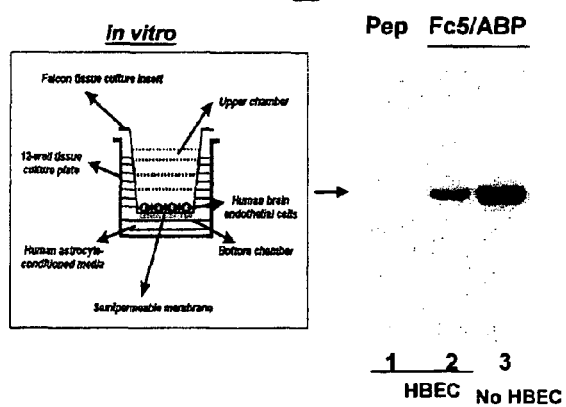

Aβ-BINDING PROTEIN AND ITS PEPTIDE DERIVATIVES AND USES THEREOF

This is a national phase entry application claiming the benefit of PCT application No. PCT/CA2006/000990, which claims priority to U.S. Provisional Patent Application No. 60/691,248 Filed Jun. 17, 2005.

FIELD OF THE INVENTION

The invention relates to a protein and its peptide derivatives having protein kinase C inhibiting properties and/or β-amyloid binding properties.

BACKGROUND OF THE INVENTION

Alzheimer's disease (AD) is a neurodegenerative disorder affecting Approximately 15% of the population over 65 years of age (~12 million worldwide, 4 million in US, 0.4 million in Canada), and is the predominant cause of progressive intellectual and cognitive failure in the aging population. Given the shifting demographics of our population, the impact of AD on public health is predicted to rise at least three-fold in the next 50 years. The disease claims over 100,000 lives/year, making it the $4^{th}$ leading cause of death in adults. As well, the cost of treatment and caring for these patients is estimated to be as high as $100 billion a year in the US alone. One of the hallmarks of AD is the accumulation of β-amyloid (Aβ) in the brain, particularly in senile plaques and cerebral microvessels. Although a number of proteins are associated with amyloid plaques, amyloid peptide (typically 39-43 aa in length) has been identified as the principal constituent of the plaque. A substantial body of evidence based on genetic, pathological and biochemical studies have indicated that Aβ plays a causal role in the development of AD pathology. A chronic imbalance in the production and clearance of Aβ results in its accumulation, either intra- or extra-cellularly, as amyloid, or other aggregated form. This gradual accumulation of aggregated Aβ initiates a cascade of events that include gliosis, inflammatory changes, neuritic/synaptic loss and transmitter loss, eventually leading to neuronal dysfunction and death.

Despite considerable progress in understanding the molecular mechanism of AD pathology, there are no effective drugs or treatments currently available that can prevent/cure the disease.

In AD, there is a severe loss of cholinergic neurons and consequently a decreased level of neurotransmitter acetylcholine (ACh) which is implicated in memory processing and storage. Therefore, cholinergic augmentation might improve cognition in AD. Indeed, the only FDA approved drugs for the treatment of AD are acetylcholine esterase (AChE) inhibitors that prevent the loss of ACh. However, the beneficial effects of this drug are limited, and the accompanying side-effects are problematic. The other treatments include the use of anti-oxidants such as vitamin E, non-steroidal anti-inflammatory drugs (NSAIDS), cholesterol-lowering drugs and estrogen therapy to mitigate the inflammatory effects of plaque formation and enhance neuroprotection. However, none of these treatments appear to have any long-term beneficial effects, particularly in improving cognition, behavior and function in AD patients. Clearly therefore, there is a great need for developing alternate approaches to identify potentially more effective drugs to treat AD.

The dynamic balance between the soluble and the insoluble pools of AD in the brain is regulated by increased production and by decreased clearance and/or increased uptake from the circulation. Therefore, agents that inhibit Aβ generation, inhibit its activity and/or promote its clearance have the potential to be more effective drugs to treat AD. The generation of Aβ from its precursor protein APP is achieved by sequential proteolysis of APP by proteases b and g secretases. Inhibitors of these enzymes have been shown to reduce Aβ production and are being developed as potential drugs for treating AD. Similarly agents that sequester and/or promote Aβ clearance are also being developed. Notable among these is the development of AD vaccine. Both active and passive immunization with Aβ has been shown to be effective in preventing Aβ deposition as well as clearing of preformed amyloid plaques in transgenic animal models of AD[1-3]. The principal mechanism of action of AD vaccines appears to be sequestration of circulating AR.

As mentioned above, currently there is no clinically proven drug that can prevent or cure AD. The only FDA approved drugs that are in clinical use to treat AD are the acetylcholine esterase (AChE) inhibitors. AChE is an enzyme that controls communication between nerve cells by the neurotransmitter acetylcholine. This communication is disrupted by the death of nerve cells in AD patients, and inhibitors of AChE are approved as drugs to elevate acetylcholine and aid neuronal function in these patients. However, the effects of these therapies are transient, providing temporary changes in cognition and function and do not stop the progression of the disease. In addition, other limitations of these drugs are the severe side effects, such as nausea, diarrhea, vomiting and anorexia. Similarly, alternate treatments such as antioxidants, non-steroidal anti-inflammatory drugs (NSAIDS) and estrogen therapy also do not have any long term beneficial effects, particularly in improving cognition, behavior and function in AD patients.

Currently several novel approaches to treating AD are being studied. Inhibitors of b and g secretases that prevent proteolytic cleavage of APP giving rise to Aβ peptides are being developed. However, their therapeutic efficacy in reducing Aβ burden is not yet known. Moreover, since these enzymes are also involved in the processing of other enzymes and signaling molecules such as Notch that are linked to neuronal development, these inhibitors may have serious non-specific side effects.

β-amyloid deposits are believed to strongly stimulate inherent immune response in the brain which triggers progressive inflammation, neuronal loss, and further acceleration of senile plaque formation. Immunotherapeutic approaches such as AD vaccines have been shown to be quite effective in reducing Aβ deposition and partial elimination of memory deficits in transgenic animals[1-3]. In human trials, Aβ vaccination showed significant reduction in cortical Aβ deposition, slow progression of dementia and stabilization of cognition. However, clinical trials had to be abandoned due to severe inflammatory reactions (meningo-encephalitic presentation) observed in a small number of AD patients.

SUMMARY OF THE INVENTION

A first object of the invention is to provide proteins or peptides which bind (β-amyloids. A protein, termed PK-4, and its peptide derivatives are found to have this property, which may be useful in the treatment or prevention of Alzheimer's disease.

A further object of the invention is to provide proteins or peptides which have protein kinase C inhibition properties. The protein PK-4 and some of its peptide derivatives have this property, which may be important in preventing β-amyloid toxicity.

A further object of the invention is to provide compositions for treating and preventing Alzheimer's disease, comprising proteins or peptides that bind to β-amyloids. A further object of the invention is to provide fusion proteins comprising proteins or peptides that bind to β-amyloids.

A further object of the invention is to provide methods for treating and preventing Alzheimer's disease using proteins or peptides which bind β-amyloid.

A first aspect of the invention provides for an amino acid sequence selected from the group consisting of SEQ ID NO. 1, SEQ ID NO. 2, SEQ ID NO. 3, SEQ ID NO. 4, and SEQ ID NO. 5. The amino acid sequence may be used for binding β-amyloids and for modulating β-amyloid aggregation, generation or toxicity, and may additionally have protein kinase C inhibiting properties.

A second aspect of the invention provides for an amino acid sequence selected from the group consisting of SEQ ID NO. 6, SEQ ID NO. 7, SEQ ID NO. 8, SEQ ID NO. 9, SEQ ID NO. 10, SEQ ID NO. 11, SEQ ID NO.12, SEQ ID NO. 13, SEQ ID NO. 14, SEQ ID NO. 15, SEQ ID NO.16, SEQ ID NO. 17, SEQ ID NO. 18 and SEQ ID NO. 19. The amino acid sequence may be used for binding β-amyloids and for modulating β-amyloid aggregation, generation or toxicity, and may additionally have protein kinase C inhibiting properties.

A third aspect of the invention provides for amino acid sequences derived from SEQ ID NO:1. These may be used for binding β-amyloids and for modulating β-amyloid aggregation, generation or toxicity, and may additionally have protein kinase C inhibiting properties.

A further aspect of the invention provides for a fusion protein or peptide comprising an amino acid sequence selected from SEQ ID NO. 1 through SEQ ID NO. 19 or an amino acid sequence derived from SEQ ID NO.1 and further comprising a cell-permeable peptide or a blood brain barrier permeable agent.

A further aspect of the invention provides for a pseudo-vaccine comprising an amino acid sequence selected from SEQ ID NO. 1 through SEQ ID NO. 19 or an amino acid sequence derived from SEQ ID NO.1 and further comprising a pharmaceutically acceptable diluent, carrier, vehicle or excipient. The amino acid sequence may be in the form of a fusion protein in which the amino acid sequence is conjugated to a cell-permeable peptide or a blood-brain barrier permeable agent. The pseudo vaccine may be used to prevent the symptoms of Alzheimer's disease.

A further aspect of the invention provides for a composition comprising an amino acid sequence selected from SEQ ID NO. 1 through SEQ ID NO. 19 or an amino acid sequence derived from SEQ ID NO.1 and further comprising a pharmacologically acceptable carrier. Such composition may be used for ameliorating the symptoms of Alzheimer's disease or for modulating protein kinase C activity.

A further aspect of the invention provides for a method of reducing the susceptibility of humans to the symptoms of Alzheimer's disease comprising the step of exposing a human to a sufficient amount of a pseudo-vaccine comprising an amino acid sequence selected from SEQ ID NO. 1 through SEQ ID NO. 19 or an amino acid sequence derived from SEQ ID NO.1 and further comprising a pharmaceutically acceptable diluent, carrier, vehicle or excipient so as to reduce the susceptibility of the human to the symptoms of Alzheimer's disease.

A further aspect of the invention provides for a method of ameliorating the symptoms of Alzheimer's disease in a subject comprising the step of introducing a composition comprising an amino acid sequence selected from SEQ ID NO. 1 through SEQ ID NO. 19 or an amino acid sequence derived from SEQ ID NO.1 and a pharmacologically acceptable carrier into the subject's body.

A further aspect of the invention provides for a method of modulating protein kinase C activity in a subject comprising the step of introducing a composition comprising an amino acid sequence selected from SEQ ID NO. 1 through SEQ ID NO. 19 or an amino acid sequence derived from SEQ ID NO.1 and a pharmacologically acceptable carrier into the subject's body.

BRIEF DESCRIPTION OF THE DRAWINGS

FIG. 9 illustrates the ability of p4, p5 and p4-5 peptides to reduce β-amyloid burden in the brains of Alzheimer's Disease transgenic mice FIG. 12 illustrates the conjugation of $p_{4-5}$ peptide to blood-brain barrier (BBB)-permeable single-domain antibody, the ability of the conjugate to bind β-amyloid like the parent peptide, and cross the BBB in vitro.

DETAILED DESCRIPTION OF THE INVENTION

There is a need for proteins or peptides that can selectively prevent or reverse the assembly or growth of β-amyloid aggregates and β-amyloid neurotoxicity.

There is disclosed herein a novel polypeptide (21 kDa) that binds physiologically relevant Aβ with high affinity (at nM range) in vitro. This polypeptide, termed PK-4, was initially isolated as a PKC inhibitor using a Phage Display system expressing human brain cDNA library. The cDNA has been cloned and PK-4 expressed as a recombinant polypeptide conjugated to His-Tag at the N-terminus.

Figure 1:
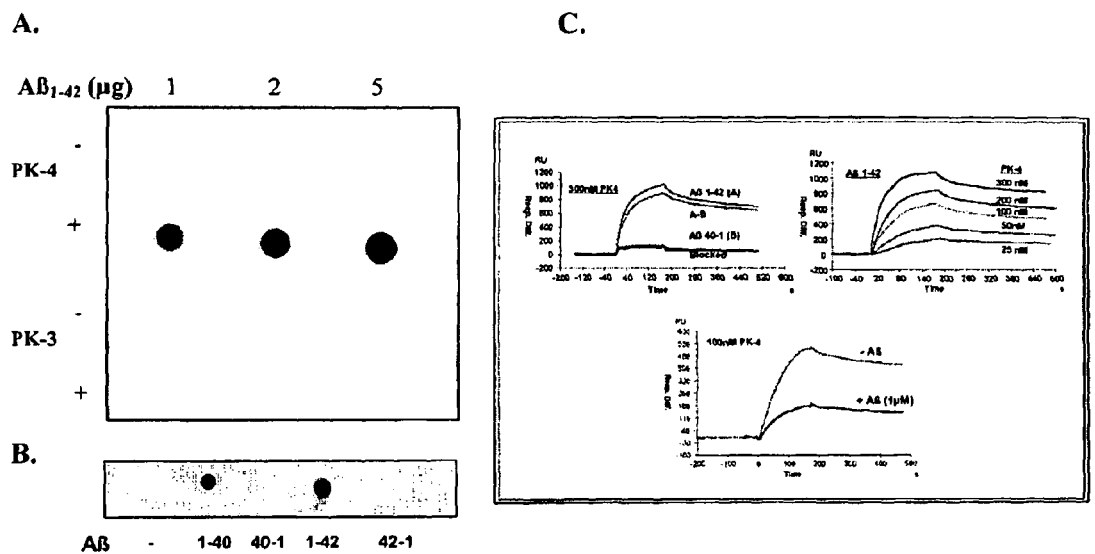
FIG. 1 illustrates the β-amyloid binding properties of PK-4 which has been isolated using phage display technique, as shown by dot blot with His-Tag antibody (FIG. 1A), dot blot with PK-4-specific antibody (FIG. 1B), and Biacore analysis (FIG. 1C).

Recombinant PK-4 (SEQ. ID. NO. 1): SGKTEYMAFPK-PFESSSSIGAEKPRNKKLPEEEVESSRT-PWLYEQEGEVEKP FIKTGFSVSVEKSTSSNRKN-QLDTNGRRRQFDEESLESFSSMPDPVDPTTVT KTFKTRKASAQASLASKDKTPK- SKSKKRNSTQLKSRVKNITHARRILQQSNRN ACNEA-
PETGSDFSMFEA), but not PK-3 (another protein isolated
using Phage Display technology), selectively binds $A\beta_{1-42}$
(FIG. 1A). PK-4 binds physiologically relevant β-amyloids,
including $A\beta_{1-42}$ and $A\beta_{1-40}$ that are implicated in AD pathology with high affinity (nM range). It does not bind the reverse
peptide $A\beta_{42-1}$ or $A\beta_{40-1}$ (FIG. 1B). High affinity-binding of
$AB_{1-42}$, but not the reverse peptide $A\beta_{40-1}$ has been confirmed
by Biacore analysis (FIG. 1C). Aβ-binding of recombinant
proteins PK-4 and PK-3 with N-terminus His-tag was determined by dot-blot assay using His-Tag antibody (A) or PK-4-
specific antibody (B), and by Biacore analysis (C). β-binding
PK-4 is a 170 amino acid-long polypeptide that corresponds
to sequence 1171-1314, and 1369-1380, of the human pericentriolar material protein-1, PCM-1.

Figure 2C:
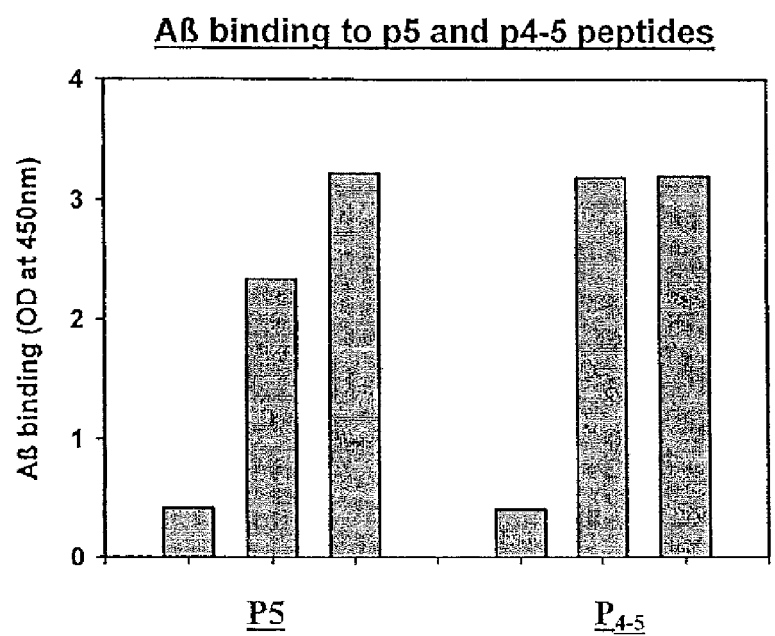
FIG. 2 illustrates the mapping of the β-amyloid binding domain of PK-4 through the generation of overlapping peptides (FIG. 2A) and β-amyloid binding properties of these peptides by dot blot (FIG. 2B) and ELISA (FIG. 2C)

The Aβ-binding domain on PK-4 has been mapped (FIG.
2A). Shorter peptides P4 (SEQ. ID. NO. 2): FSSMPD-
PVDPTTVTKTFKTRKASAQASLASKDKTPKSKSK), P5
(SEQ. ID. NO. 3: KDKTPKSKSKKRNSTQLK-
SRVKNITHARRILQQSNRNACN) and $P_{4-5}$ (SEQ. ID No. 4
KTFKTRKASAQASLASKDKTPK-
SKSKKRNSTQLKSRVKNI) all bind Aβ with high affinity
(nM range) as determined by dot blot (FIG. 2B) and ELISA
assays (FIG. 2C) using antibodies selective to respective peptides and Aβ. $A\beta_{1-42}$ spotted on dot blot and p4 and p5 binding
to Aβ was determined using p4- and p5-specific antibodies
developed in-house (dot blot). For ELISA, Peptides were
coated on ELISA plates, incubated with 100 nM Aβ and its
binding to peptides was determined using Aβ-specific antibody.

Figure 3:
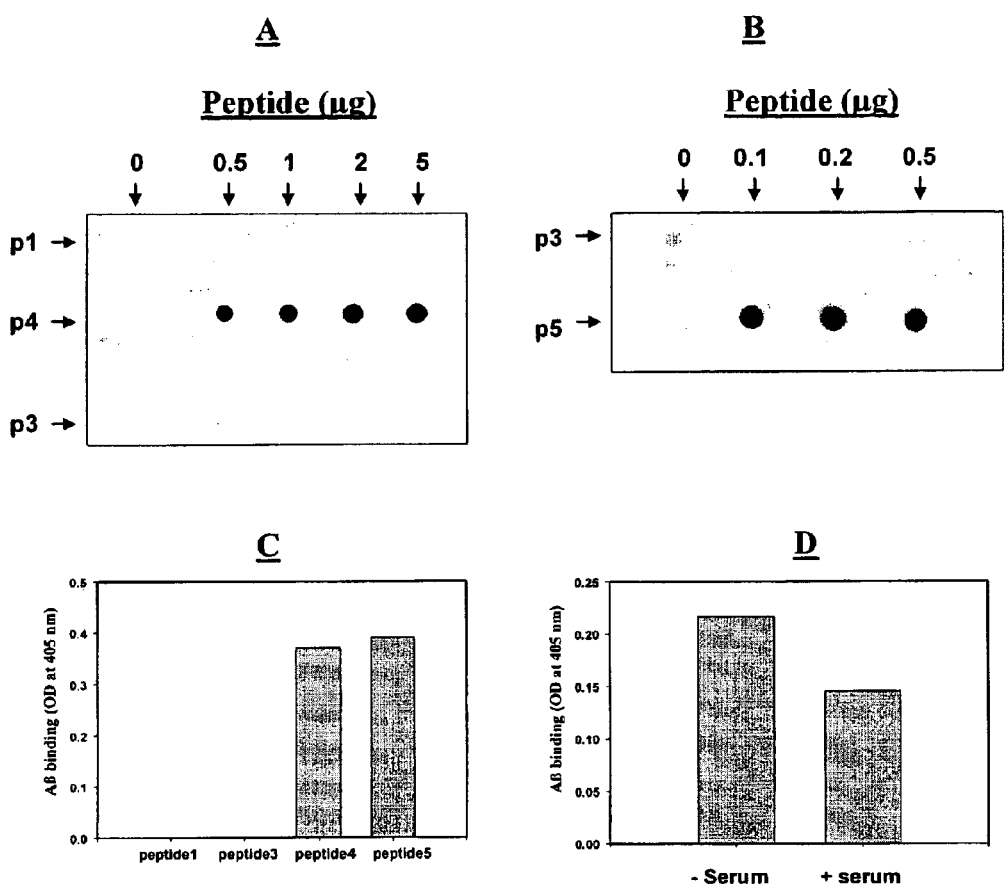
FIG. 3 illustrates the selective binding and β-amyloid sequestration of peptides p4 and p5, as shown by dot blot (FIGS. 3A and 3B) and ELISA (FIGS. 3C and 3D)

This binding is specific as other peptides of same size
derived from PK-4 (peptides P1 and P3) do not bind Aβ
(FIGS. 3A, 3B and 3C). Both P4 and P5 are able to bind Aβ
even in the presence of serum proteins (FIG. 3D). Peptides
were spotted on nitrocellulose paper (dot-blot) or ELISA
plate and incubated with 100 nM $A\beta_{1-42}$ and Aβ binding was
determined using an Aβ-selective antibody Nucleotide sequences of PK-4 and its derivative peptides
P4, P5 and P4-5 are as follows:

```
PK-4 (SEQ ID NO: 20):
tcaggaaaaacagaatatatggcttttccaaaaccttttgaaagcagt tcctctattggagcagagaaaccaaggaataaaaaactgcctgaagag gaggtggaaagcagtaggacaccatggttatatgaacaagaaggtgaa gtagagaaaccatttatcaagactggattttcagtgtctgtagaaaaa tctacaagtagtaaccgcaaaaatcaattagatacaaacggaagaga cgccagtttgatgaagaatcactggaaagctttagcagtatgcctgat ccagtagatccaacaacagtgactaaaacattcaagacaagaaaagcg tctgcacaggccagcctggcatctaaagataaaactcccaagtcaaaa agtaagaagaggaattctactcagctgaaaagcagagttaaaaacatc acacatgctaggagaatactacagcagtctaacagaaatgcatgcaat gaagcgccagaaactgggagtgattttccatgtttgaagct P4 (SEQ ID NO: 21)
tttagcagtatgcctgatccagtagatccaacaacagtgactaaaaca ttcaagacaagaaaagcgtctgcacaggccagcctggcatctaaagat aaactcccaagtcaaaaagtaag
```

```
P5 (SEQ ID NO: 22)
Aaagataaaactcccaagtcaaaaagtaagaagaggaattctactcag ctgaaaagcagagttaaaaacatcacacatgctaggagaatactacag cagtctaacagaaatgcatgcaat P4-5 (SEQ ID NO: 23)
Aaaacattcaagacaagaaaagcgtctgcacaggccagcctggcatct aaagataaaactcccaagtcaaaaagtaagaagaggaattctactcag ctgaaaagcagagttaaaaacatc
```

Further derivative peptides that are likely to have similar
Aβ binding properties to PK-4, P4, P5 and P4-5 (as they are
shorter peptides from the putative Aβ binding region of PK-4)
are as follows:

| | |
|---|---|
| KDKTPKSKSK | (SEQ. ID. NO. 5) |
| DKTPKSKSK | (SEQ. ID. NO. 6) |
| KTPKSKSK | (SEQ. ID. NO. 7) |
| TPKSKSK | (SEQ. ID. NO. 8) |
| KDKTPKSKS | (SEQ. ID. NO. 9) |
| KDKTPKSK | (SEQ. ID. NO. 10) |
| KDKTPKS | (SEQ. ID. NO. 11) |
| KDKTPK | (SEQ. ID. NO. 12) |
| DKTPKSKS | (SEQ. ID. NO. 13) |
| DKTPKSK | (SEQ. ID. NO. 14) |
| DKTPKS | (SEQ. ID. NO. 15) |
| KTPKSKS | (SEQ. ID. NO. 16) |
| KTPKSK | (SEQ. ID. NO. 17) |
| KTPKS | (SEQ. ID. NO. 18) |
| TPKSK | (SEQ. ID. NO. 19) |

Additional peptides derived from PK-4 are likely to have
useful properties as well, particularly those derived from or
comprising portions of the Aβ-binding domain of PK-4 and
additionally retaining Aβ-binding functions. Such shorter
peptides may be useful as they are easier and cheaper to
synthesize, and may also be more easily absorbed into the
human body. Similarly, it is expected that peptides having a
high degree of homology with PK-4 or its derivative peptides
(preferably 90% homology or more) and having Aβ-binding
function will also be useful. Modifications to PK-4 and its
derivatives may also be made, such as methylation, acetylation, amidation and cyclization, in order to determine if such
changes increase the efficacy of ABPs in inhibiting Aβ activity and/or increase the in vivo stability and bio-availability of
ABPs (i.e., pharmacokinetics or pharmacodynamics of
ABPs). These derivatives can be created during the generation of synthetic ABPs. Also, with further studying of the
Aβ-interacting domain on ABPs, amino acids may be incorporated or deleted to create novel peptide sequences that may
be much more potent in terms of binding properties.

Figure 4:
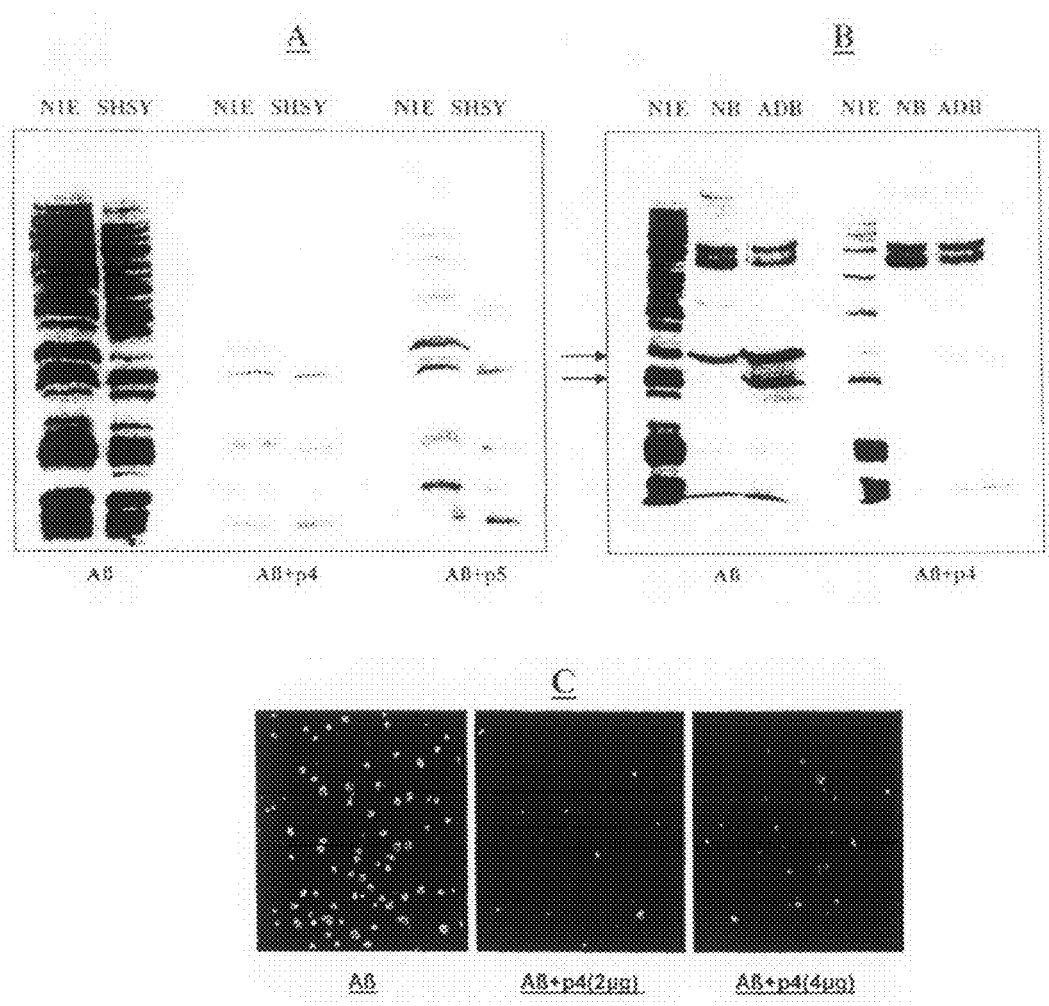
FIG. 4 illustrates the inhibition of β-amyloid binding to cellular protein by peptides p4 and p5, as shown by overlay assay (FIGS. 4A and 4B) and fluorescence assay (FIG. 4C)

Peptides P4, P5 and $P_{4-5}$ (data not shown) all inhibit the
binding of Aβ to proteins from mouse and human neuroblastoma cells in in vitro over-lay assays (FIG. 4A). Most importantly, these peptides also inhibit Aβ interaction with human
brain proteins from normal (NB) and Alzheimer's disease patients (FIG. 4B). Consistent with their ability to inhibit Aβ binding to proteins from primary rat cortical neurons (data not shown), they inhibit cellular association and uptake of Aβ by primary neurons (FIG. 4C, reduction in the number of cells with green fluorescence). The ability of p4 and p5 peptides to interfere with Aβ interaction with cellular proteins (mouse neuroblastoma cells, N1E; human neuroblastoma cells, SHSY; and normal, NB and Alzheimer's, ADB, human brain tissue) in vitro was determined by Aβ overlay assay on protein trans-blots using Aβ-specific antibody (A). Aβ uptake was determined by incubating primary cortical neurons with fluorescent Aβ, FITC-Aβ [green fluorescence] (B).

Figure 5:
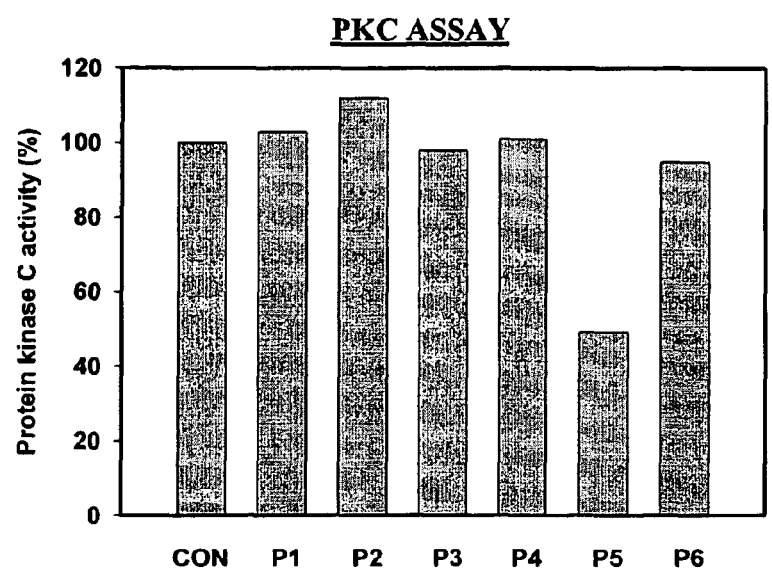
FIG. 5 illustrates the mapping of PKC inhibitory activity in PK-4 protein to peptide 5 sequence

Peptide P5, like its parent protein PK-4, also inhibits Protein Kinase C, a key cell signaling enzyme (see FIG. 5). Various synthetic peptides derived from PK-4 (see FIG. 2) were tested for PKC inhibitory activity in vitro using rat brain PKC. As shown in FIG. 5, only peptide 5 (P5) exhibited PKC inhibitory activity. Other peptides, P1, P2, P3, P4, and P6, had no effect on PKC, indicating that PKC-inhibitory activity in PK-4 protein resided in the P5 peptide domain.

Figure 6:
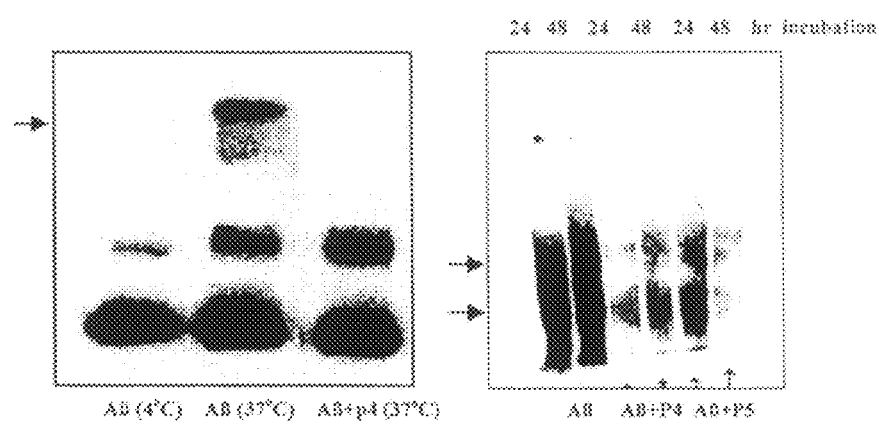
FIG. 6 illustrates the interference with β-amyloid aggregation by p4 and p5 peptides, as shown by western blot analysis

Aβ is known to aggregate and form higher oligomeric and insoluble fibrillar forms when incubated at 37° C. These aggregated forms are believed to be the toxic form of Aβ. The presence of P4 (SEQ. ID. NO. 2) and P5 (SEQ. ID. NO. 3) peptides appear to interfere with Aβ aggregation and potentially reduce the formation of toxic Aβ aggregates (FIG. 6). $Aβ_{1-42}$ was incubated with equimolar concentration of P4 or P5 peptides for various lengths of time and Aβ aggregation was determined by western blot analysis using Aβ-specific antibody. The presence of P4 or P5 peptide reduced the amount of aggregated forms of Aβ.

Figure 7:
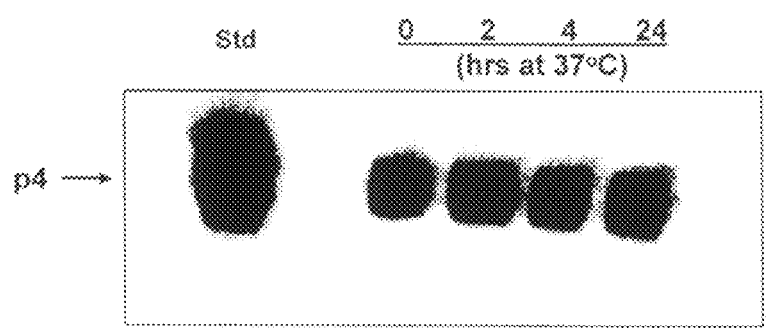
FIG. 7 illustrates the in vitro stability of peptide p4 in 10% serum, as shown by western blot analysis

All peptides P4, P5 and $P_{4-5}$ are stable in serum containing medium for up to 48 hrs and also in rat blood plasma (FIG. 7). P4 peptide was incubated in culture medium containing 10% fetal calf serum for various time periods at 37° C. and the stability of p4 was tested by Western blot analysis using p4-specific antibody. No loss of P4 was detected over a 24 hour period.

Figure 8:
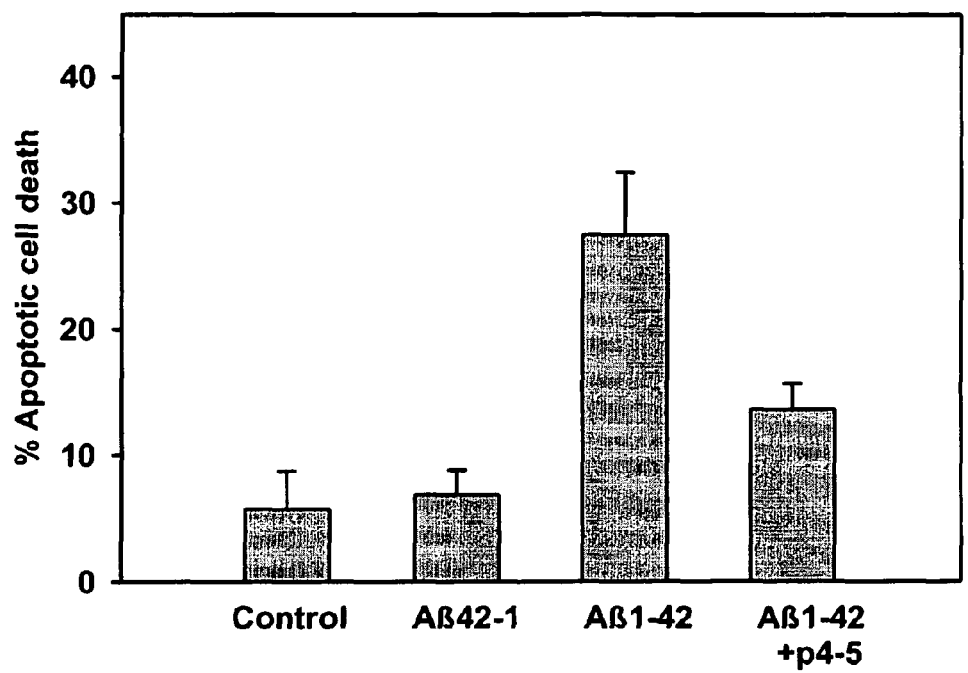
FIG. 8 illustrates the protection of human neuro-blastomas cells against β-amyloid toxicity by peptide p4-5.

Peptides P4 and $P_{4-5}$ showed no toxicity in vitro against cultured neuroblastoma cells and primary cortical neurons (data not shown). Most importantly, these peptides, particularly peptide $p_{4-5}$, effectively protected neuroblastoma cells against Aβ-induced toxicity (FIG. 8). Human neuroblastoma cells, SH-SY5Y were treated with 15 μM Aβ in the presense or absence of Aβ binding peptide $p_{4-5}$ in serum-free medium for 48 hrs and cell death was assessed by Hoechst stain. Peptide $p_{4-5}$ was quite effective in blocking Aβ toxicity at 30 μM concentration.

Further, none of the peptides, p4, p5, or p4-5 showed any apparent toxicity in vivo in CD-1 mice up to 20 mg/kg body weight. Most importantly, preliminary data indicate that these peptides reduce brain Aβ burden in a transgenic animal model of Alzheimer's Disease when administered subcutaneously (FIG. 9). Alzheimer's Disease (AD) transgenic mice were administered either vehicle (saline) or Aβ binding peptides, ABPs ($P_4$, $P_5$ or $P_{4-5}$) subcutaneously every second day for two months. At the end of the treatment period animals were sacrificed and brain sections were stained for Aβ deposition using Aβ-specific antibody (6E10). As can be seen in FIG. 9, preliminary results indicate that administration of ABPs reduces the accumulation of Aβ in the brains of these animals.

Figure 10:
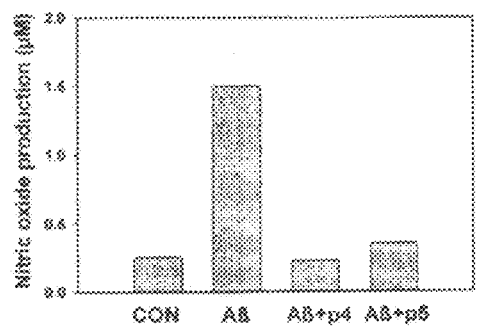
FIG. 10 illustrates the ability of p4 and p5 peptides to prevent β-amyloid-induced oxidative stress (nitric oxide production) in human astrocytes
Figure 11:
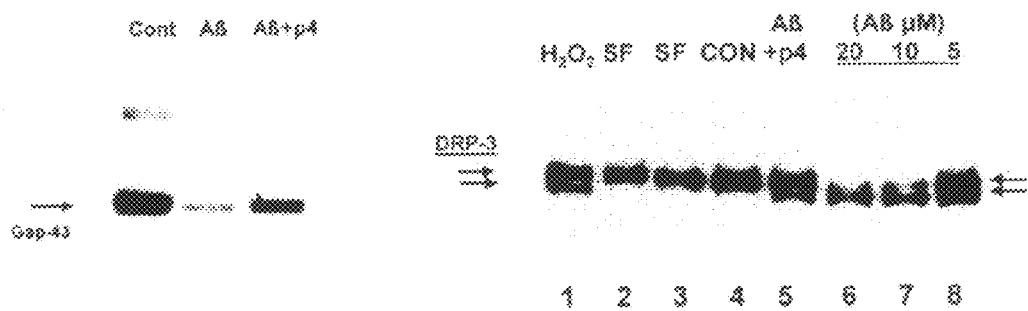
FIG. 11 illustrates the ability of p4 peptides to block β-amyloid-induced breakdown of synaptic proteins in rat primary neurons

These peptides can sequester Aβ from solutions containing up to 30% serum. They can block Aβ-induced oxidative stress, expression of inflammatory genes, and loss of synaptic proteins (Gap-43, DRP-3) in primary cells of brain origin (FIG. 10, FIG. 11). Human astrocytes were exposed to $Aβ_{25-35}$ in the presence or absence of P4 or P5, and NO generation was measured. As shown in FIG. 10, ABPs inhibit Aβ-induced oxidative stress in these cells. Primary rat cortical neurons were exposed to $Aβ_{1-42}$ in the presence or absence of P4 peptide and levels of Gap-43 and DRP-3 were measured by western blot. P4 partially blocked the Aβ-induced breakdown of Gap-43 (FIG. 11A) and DRP-3 (FIG. 11 B, compare lane 5, Aβ+P4, with lane-6, Aβ20 μM). Thus, these peptides may act as a 'sink' to reduce the availability of unbound Aβ in culture media.

By way of non-limiting example, these peptides and analogues and variants thereof can be used as "decoy" peptides to disrupt the pathological interaction of Aβ with intra- or extracellular proteins. Aβ-binding peptides (ABPs) can be engineered to cross biological membranes and access intracellular Aβ by generating fusion proteins with cell-permeable peptides[4,5]. Examples of cell-permeable peptides suitable for this purpose are as follows: TAT-peptide (YGRKKRRQRRR) (SEQ ID NO: 24); Penetratin (RQIKIWFQNRRMKWKK) (SEQ ID NO: 25); Poly arginine (7-11 residues, RRRRRRRRRRR) SEQ ID NO: 26; VP22 (DAATATRGR-SAASRPTQRPRAPARSASRPRRPVQ) (SEQ ID NO: 27); Transportan (GWTLNSAGYLLGKINLKALAALAKKIL) (SEQ ID NO: 28); MAP (KLALKLALKALKAALKLA) (SEQ ID NO: 29); MTS (AAVALLPAVLLALLP) (SEQ ID NO: 30); and PEP-1 (KETWWETWWTEWSQPKKKRKV) (SEQ ID NO: 31).

These cell-permeable peptides can be conjugated to ABP peptides during peptide synthesis. They may be attached either on the N- or C-terminus region or can be generated as a recombinant conjugates by generating cDNA and cloning using molecular biology tools.

In addition, Aβ-binding peptides or their cell-permeable fusion proteins can be conjugated with blood brain barrier "BBB" permeable agents such as single domain antibodies (e.g. U.S. patent application Ser. No. 10/031,874, filed 25 May 2001), anti-transferrin receptor antibodies or anti-insulin receptor antibodies. These antibodies may be conjugated to ABPs using recombinant technology as described for sdAb or avidin/streptavidin technology. (see William M. Pardridge. The American Society for Experimental NeuroTherapeutics, Inc. NeuroRx. 2005 January; 2(1): 129-138).

These fusion proteins can be used not only to specifically deliver ABPs to the brain but also inside brain cells. This is particularly important since intracellular Aβ is believed to play a major role in synaptic dysfunction and neurodegeneration well before the accumulation of insoluble Aβ in senile plaques[6,7]. Such pseudo vaccines would be administered, for example, subcutaneously, and further ingredients beyond a pharmacologically acceptable carrier would not be necessary. For example, peptide $P_{4-5}$ has been conjugated to "BBB" permeable single-domain antibody FC5 and it has been shown that the peptide crosses blood-brain barrier in vitro, and that conjugation does not affect the peptide's ability to bind Aβ (FIG. 12). Recombinant Aβ binding peptide $P_{4-5}$ (rABP, His-tag-MPDPVDPTTVTKTFK-TRKASAQASLASKDKTPKSKSKKRNSTQLKSRVKNI) was conjugated to BBB-permeable single-domain antibody FC5 (FIG. 8A). The FC5 conjugated peptide (FC5/ABP) bound $AB_{1-42}$ equally well as the synthetic (sABP) or non-conjugated peptide (rABP) (FIG. 8B). In an in vitro BBB assay (FIG. 8C) it was shown that non-conjugated $P_{4-5}$ (rABP) did not cross the BBB, however it crossed the barrier when conjugated to FC5 (compare lane 1 and 2 in FIG. 8C), indicating that FC5 conjugation facilitates $P_{4-5}$-crossing of BBB in vitro.

The peptides described herein may also be used as a "sink" to sequester and facilitate the clearing of soluble Aβ to reduce Aβ burden. Several recent studies have suggested that the principal mechanism by which AD vaccines reduce Aβ burden is by sequestering circulating Aβ[11,12].

The Aβ-sequestering, neuroprotective and anti-inflammatory properties of Aβ-binding peptide (ABP) are useful to create cell- and BBB-permeable Aβ pseudo-vaccines. Such 'vaccines' combine several unique properties not achievable by direct or indirect immunization approaches with Aβ, Aβ fragments, or their respective antibodies. These properties include the ability of ABP to: a) sequester peripheral Aβ, b) access the brain and counteract central effects of Aβ and c) modulate innate inflammatory responses in the brain without inducing cytotoxic T cell immunity, a major disadvantage with the current AD vaccine.

As mentioned earlier, PK-4 has another activity, that is it can inhibit a key cell signaling enzyme, protein kinase C (PKC). It has been determined that the PKC-inhibitory domain resides in peptide P5 (data not shown), which also binds Aβ. Protein kinase C plays a key role in Aβ toxicity, and the fact that P5 has dual function of binding Aβ and also inhibit PKC activity makes it a potentially unique molecule to counter Aβ toxicity. This also distinguishes it from Aβ vaccine in this respect.

Protein Kinase C (PKC) is a key cell signaling enzyme implicated in a variety of cellular functions. Its hyperactivity has been linked to a number of diseases, including cancer and diabetes. As a consequence, PKC inhibitors are being developed as potential therapeutics to treat these diseases, and the peptides disclosed herein may have such potential.

Although the cDNA sequence of PK-4 indicates high homology to a known mammalian protein (pericentriolar material-1, PCM-1) it does not represent any known Aβ-binding proteins described in the literature.

It is understood that the examples described above in no way serve to limit the true scope of this invention, but rather are presented for illustrative purposes.

REFERENCES

The inclusion of a reference is neither an admission nor a suggestion that it is relevant to the patentability of anything disclosed herein.

1. Golde, T. E. (2003) Alzheimer disease therapy: Can the amyloid cascade be halted? *J. Clin. Invest.* 111, 11-18.
2. Monsonego A, and Weiner H L (2003) Immunotherapeutic approaches to Alzheimer's disease *Science.* 302, 834-838.
3. Bard F et. al. (2000) Peripherally administered antibodies against amyloid beta-peptide enter the central nervous system and reduce pathology in a mouse model of Alzheimer disease *Nat Med.* 6, 916-919
4. Joliot, A. and Prochiantz, A. (2004) Transduction peptides: from technology to physiology *Nat. Cell Biol.* 6, 189-196.
5. Zhao, M. and Weissleder R. (2004) Intracellular cargo delivery using tat peptide and derivatives *Med. Res. Rev.* 24, 1-12.
6. D'Andrea M R, Nagele R G, Wang H Y, Lee D H. (2002) Consistent immunohistochemical detection of intracellular beta-amyloid 42 in pyramidal neurons of Alzheimer's disease entorhinal cortex. *Neurosci Lett.* 333:163-166.
7. McLean C A, Cherny R A, Fraser F W, Fuller S J, Smith M J, Beyreuther K, Bush A I, Masters C L. (1999) Soluble pool of Abeta amyloid as a determinant of severity of neurodegeneration in Alzheimer's disease. *Ann Neurol.* 46:860-866

What is claimed is:

1. An isolated polypeptide comprising an amino acid sequence having at least 90% sequence identity to SEQ ID NO:1 that inhibits β-amyloid aggregation or toxicity.

2. The isolated polypeptide of claim 1 for use in binding β-amyloids.

3. The isolated polypeptide of claim 2 having protein kinase C inhibition properties.

4. A composition comprising the isolated polypeptide of claim 1 and a pharmacologically acceptable carrier.

5. An isolated soluble polypeptide comprising SEQ ID NO:1.

6. The isolated soluble polypeptide of claim 5 for use in binding β-amyloids.

7. The isolated soluble polypeptide of claim 5 wherein the polypeptide is methylated, acetylated, amidated and/or cyclized.

8. A fusion protein comprising at least one of the isolated soluble polypeptide of claim 5 and a cell-permeable peptide selected from the group consisting of HIV-1 Trans-activating Transcriptional Activator Peptide (YGRKKRRQRRR); Penetratin (RQIKIWFQNRRMKWKK); Poly arginine having 7-11 residues; Herpes Simplex Virus Tegument Protein (DAATATRGRSAASRPTQRPRAPARSASRPRRPVQ); Transportan (GWTLNSAGYLLGKINLKALAALAKKIL); Multiple Antigen Peptide (KLALKLALKALKAALKLA); Membrane-Translocating Sequence of Human Fibroblast Growth Factor (AAVALLPAVLLALLP) and Cell-Penetrating Peptide PEP-1(KETWWETWWTEWSQPKKKRKV).

9. A pharmaceutical composition comprising the fusion protein of claim 8 and a pharmaceutically acceptable diluent, carrier, vehicle or excipient for ameliorating symptoms of Alzheimer's disease.

10. A fusion protein comprising at least one of the isolated soluble polypeptide of claim 5 and a blood-brain barrier permeable agent wherein the blood-brain barrier permeable agent is a single-domain antibody, an anti-transferrin receptor antibody or an anti-insulin receptor antibody.

11. The fusion protein of claim 10 wherein the blood-brain barrier permeable agent is a single domain antibody FC5.

12. A pharmaceutical composition comprising the fusion protein of claim 10 and a pharmaceutically acceptable diluent, carrier, vehicle or excipient for ameliorating the symptoms of Alzheimer's disease.

13. A pharmaceutical composition comprising the isolated soluble polypeptide of claim 5 and a pharmaceutically acceptable diluent, carrier, vehicle or excipient.

14. The pharmaceutical composition of claim 13 for use in inhibiting β-amyloid aggregation or toxicity.

15. The pharmaceutical composition of claim 13 for ameliorating symptoms of Alzheimer's disease.

16. A kit comprising the pharmaceutical composition of claim 13.

17. A method of ameliorating symptoms of Alzheimer's disease comprising the step of introducing a sufficient amount of the pharmaceutical composition of claim 13 into the subject's body to ameliorate symptoms of Alzheimer's disease.

18. A method of ameliorating the symptoms of Alzheimer's disease in a subject comprising the step of introducing the pharmaceutical composition of claim 13 into the subject's body.

19. A method of modulating protein kinase C activity in a subject comprising the step of introducing the pharmaceutical composition of claim 13 into the subject's body.

20. A method of modulating protein kinase C activity in a subject comprising the step of introducing the pharmaceutical composition of claim 9 into the subject's body.

* * * * *

SEQUENCE LISTING

```
<160> NUMBER OF SEQ ID NOS: 32

<210> SEQ ID NO 1
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Gly Lys Thr Glu Tyr Met Ala Phe Pro Lys Pro Phe Glu Ser Ser
  1               5                  10                  15

Ser Ser Ile Gly Ala Glu Lys Pro Arg Asn Lys Lys Leu Pro Glu Glu
             20                  25                  30

Glu Val Glu Ser Ser Arg Thr Pro Trp Leu Tyr Glu Gln Glu Gly Glu
         35                  40                  45

Val Glu Lys Pro Phe Ile Lys Thr Gly Phe Ser Val Ser Val Glu Lys
     50                  55                  60

Ser Thr Ser Ser Asn Arg Lys Asn Gln Leu Asp Thr Asn Gly Arg Arg
 65                  70                  75                  80

Arg Gln Phe Asp Glu Glu Ser Leu Glu Ser Phe Ser Ser Met Pro Asp
                 85                  90                  95

Pro Val Asp Pro Thr Thr Val Thr Lys Thr Phe Lys Thr Arg Lys Ala
            100                 105                 110

Ser Ala Gln Ala Ser Leu Ala Ser Lys Asp Lys Thr Pro Lys Ser Lys
        115                 120                 125
```

```
Ser Lys Lys Arg Asn Ser Thr Gln Leu Lys Ser Arg Val Lys Asn Ile
    130                 135                 140

Thr His Ala Arg Arg Ile Leu Gln Gln Ser Asn Arg Asn Ala Cys Asn
145                 150                 155                 160

Glu Ala Pro Glu Thr Gly Ser Asp Phe Ser Met Phe Glu Ala
                165                 170

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Ser Ser Met Pro Asp Pro Val Asp Pro Thr Thr Val Thr Lys Thr
  1               5                  10                  15

Phe Lys Thr Arg Lys Ala Ser Ala Gln Ala Ser Leu Ala Ser Lys Asp
                20                  25                  30

Lys Thr Pro Lys Ser Lys Ser Lys
            35                  40

<210> SEQ ID NO 3
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Asp Lys Thr Pro Lys Ser Lys Ser Lys Arg Asn Ser Thr Gln
  1               5                  10                  15

Leu Lys Ser Arg Val Lys Asn Ile Thr His Ala Arg Arg Ile Leu Gln
                20                  25                  30

Gln Ser Asn Arg Asn Ala Cys Asn
            35                  40

<210> SEQ ID NO 4
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Thr Phe Lys Thr Arg Lys Ala Ser Ala Gln Ala Ser Leu Ala Ser
  1               5                  10                  15

Lys Asp Lys Thr Pro Lys Ser Lys Ser Lys Arg Asn Ser Thr Gln
                20                  25                  30

Leu Lys Ser Arg Val Lys Asn Ile
            35                  40

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Lys Asp Lys Thr Pro Lys Ser Lys Ser Lys
  1               5                  10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Lys Thr Pro Lys Ser Lys Ser Lys
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Thr Pro Lys Ser Lys Ser Lys
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Pro Lys Ser Lys Ser Lys
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Asp Lys Thr Pro Lys Ser Lys Ser
  1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Asp Lys Thr Pro Lys Ser Lys
  1               5

<210> SEQ ID NO 11
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 11

Lys Asp Lys Thr Pro Lys Ser
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Asp Lys Thr Pro Lys
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Lys Thr Pro Lys Ser Lys Ser
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Lys Thr Pro Lys Ser Lys
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Lys Thr Pro Lys Ser
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Thr Pro Lys Ser Lys Ser
 1               5

<210> SEQ ID NO 17

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Thr Pro Lys Ser Lys
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Thr Pro Lys Ser
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Pro Lys Ser Lys
 1               5

<210> SEQ ID NO 20
<211> LENGTH: 522
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
tcaggaaaaa cagaatatat ggcttttcca aaacctttg aaagcagttc ctctattgga        60
gcagagaaac caaggaataa aaaactgcct gaagaggagg tggaaagcag taggacacca      120
tggttatatg aacaagaagg tgaagtagag aaaccattta tcaagactgg attttcagtg      180
tctgtagaaa atctacaag tagtaaccgc aaaaatcaat tagatacaaa cggaagaaga       240
cgccagtttg atgaagaatc actggaaagc tttagcagta tgcctgatcc agtagatcca      300
acaacagtga ctaaaacatt caagacaaga aaagcgtctg cacaggccag cctggcatct     360
aaagataaaa ctcccaagtc aaaaagtaag aagaggaatt ctactcagct gaaaagcaga     420
gttaaaaaca tcacacatgc taggagaata ctacagcagt ctaacagaaa tgcatgcaat    480
gaagcgccag aaactgggag tgattttttcc atgtttgaag ct                        522

<210> SEQ ID NO 21
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
tttagcagta tgcctgatcc agtagatcca acaacagtga ctaaaacatt caagacaaga    60
aaagcgtctg cacaggccag cctggcatct aaagataaaa ctcccaagtc aaaaagtaag   120
```

<210> SEQ ID NO 22
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
aaagataaaa ctcccaagtc aaaaagtaag aagaggaatt ctactcagct gaaaagcaga    60
gttaaaaaca tcacacatgc taggagaata ctacagcagt ctaacagaaa tgcatgcaat   120
```

<210> SEQ ID NO 23
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
aaaacattca agacaagaaa agcgtctgca caggccagcc tggcatctaa agataaaact    60
cccaagtcaa aaagtaagaa gaggaattct actcagctga aaagcagagt taaaaacatc   120
```

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Tyr Gly Arg Lys Lys Arg Arg Gln Arg Arg Arg
  1               5                  10
```

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Arg Gln Ile Lys Ile Trp Phe Gln Asn Arg Arg Met Lys Trp Lys Lys
  1               5                  10                  15
```

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Arg Arg Arg Arg Arg Arg Arg Arg Arg Arg Arg
  1               5                  10
```

<210> SEQ ID NO 27
<211> LENGTH: 34
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 27

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Leu Ala Leu Lys Leu Ala Leu Lys Ala Leu Lys Ala Ala Leu Lys
1               5                   10                  15

Leu Ala

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ala Val Ala Leu Leu Pro Ala Val Leu Leu Ala Leu Leu Pro
1               5                   10                  15

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Glu Thr Trp Trp Glu Thr Trp Trp Thr Glu Trp Ser Gln Pro Lys
1               5                   10                  15

Lys Lys Arg Lys Val
            20
```

```
<210> SEQ ID NO 32
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Pro Asp Pro Val Asp Pro Thr Thr Val Thr Lys Thr Phe Lys Thr
 1               5                  10                  15

Arg Lys Ala Ser Ala Gln Ala Ser Leu Ala Ser Lys Asp Lys Thr Pro
            20                  25                  30

Lys Ser Lys Ser Lys Lys Arg Asn Ser Thr Gln Leu Lys Ser Arg Val
        35                  40                  45

Lys Asn Ile
     50
```